(12) United States Patent
Garito et al.

(10) Patent No.: US 7,879,032 B1
(45) Date of Patent: Feb. 1, 2011

(54) DISPOSABLE ELECTROSURGICAL HANDPIECE

(75) Inventors: Jon C. Garito, Oceanside, NY (US); Alan G. Ellman, Oceanside, NY (US)

(73) Assignee: Ellman International, Inc. NY (US)

( * ) Notice: Subject to any disclaimer, the term of this patent is extended or adjusted under 35 U.S.C. 154(b) by 960 days.

(21) Appl. No.: 11/787,245

(22) Filed: Apr. 16, 2007

(51) Int. Cl.
*A61B 18/12* (2006.01)
(52) U.S. Cl. .............................. 606/42; 606/41; 606/34
(58) Field of Classification Search ............. 606/32–35, 606/41, 4, 45–502
See application file for complete search history.

(56) References Cited

U.S. PATENT DOCUMENTS

| | | | | |
|---|---|---|---|---|
| 4,706,667 A | * | 11/1987 | Roos | 606/48 |
| 5,814,044 A | * | 9/1998 | Hooven | 606/48 |
| 6,235,027 B1 | * | 5/2001 | Herzon | 606/51 |
| 6,461,352 B2 | * | 10/2002 | Morgan et al. | 606/34 |
| 7,156,844 B2 | * | 1/2007 | Reschke et al. | 606/41 |
| 2006/0009763 A1 | * | 1/2006 | Goble et al. | 606/49 |
| 2010/0114088 A1 | * | 5/2010 | Buchman et al. | 606/33 |

\* cited by examiner

*Primary Examiner*—Michael Peffley

(57) ABSTRACT

Incorporating into an electrosurgical handpiece a device configured to disable the handpiece when a built-in usage time period expires. Preferably, the device comprises a timer in the form of an activating battery with a known discharge rate such that the battery voltage gradually reduces in value with use. The battery in turn is coupled to a circuit which monitors the battery voltage and operates a switch which decouples the handpiece electrode from the electrosurgical current source when the battery voltage falls below a preset value. This effectively disables the handpiece preventing reuse.

10 Claims, 2 Drawing Sheets

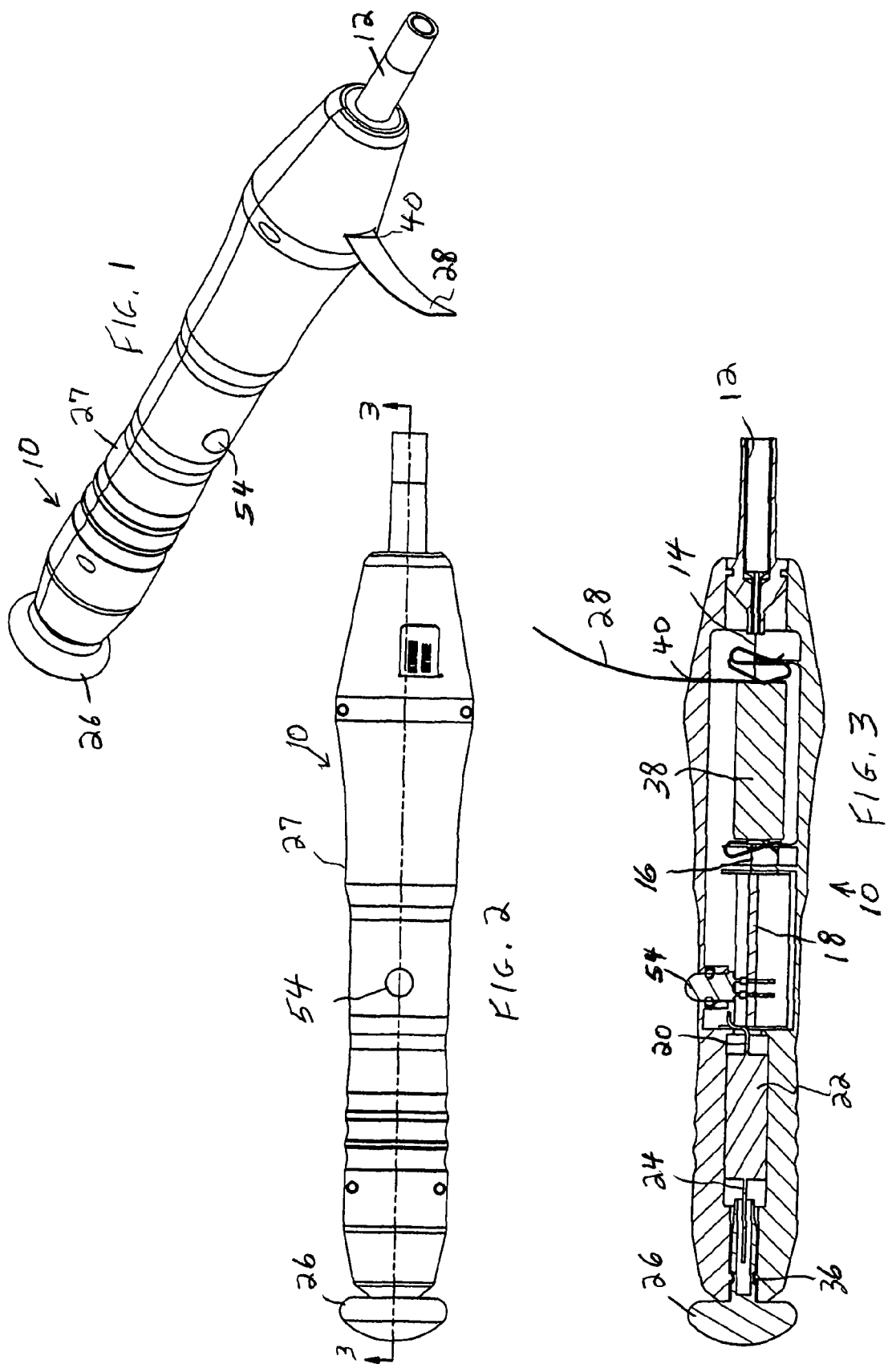

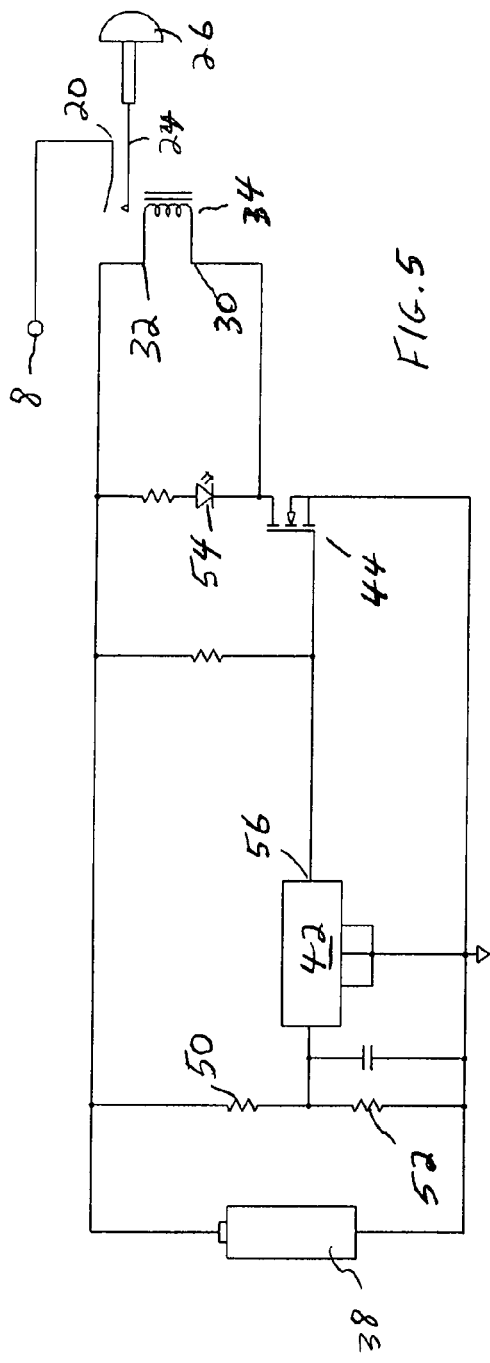
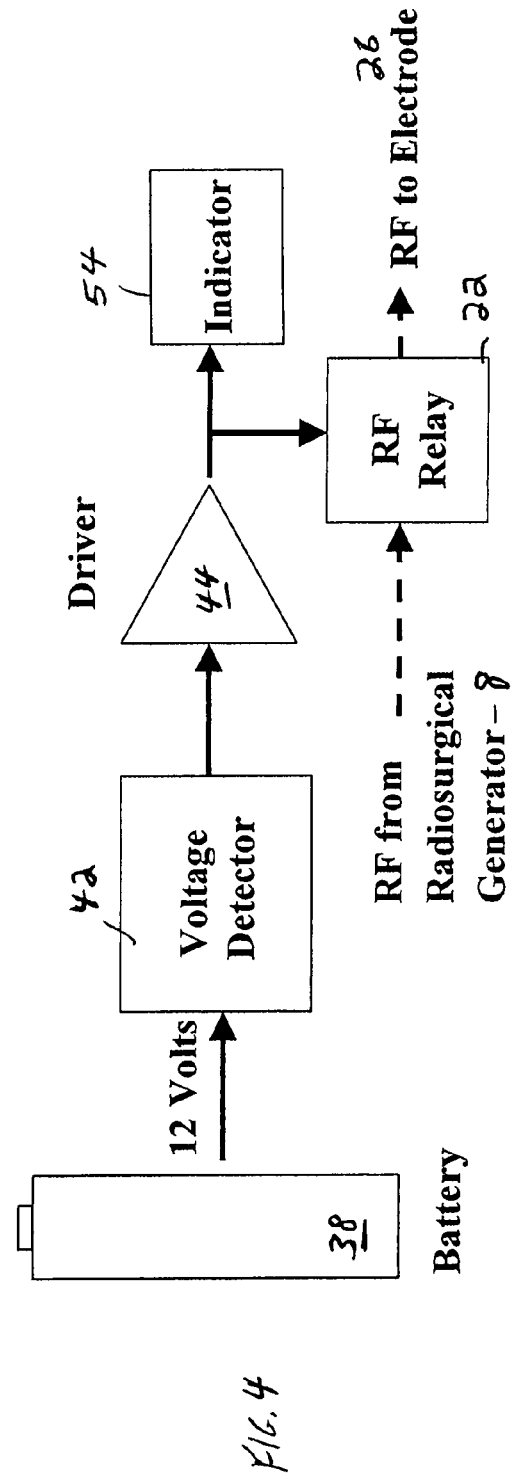
FIG. 5
FIG. 4

DISPOSABLE ELECTROSURGICAL HANDPIECE

The invention is directed to a disposable electrosurgical handpiece, and especially to a disposable electrosurgical handpiece specifically adapted for non-ablative surgery.

BACKGROUND OF INVENTION

Medical systems are designed to improve the diagnostic and surgical applications of the medical practitioners. However, due to their medical application, they also have to be safe for both the patient and operator/practitioner. There are international standards such as the IEC/EN standards, and also FDA guidelines that guide on the suggested safety measures needed of the medical system and its accessories. To achieve this safety, it is imperative that both the medical system and its associated accessories meet these safety standards/guidelines. However, the safe use of the medical system and its accessories are also dependent the responsibility of the user in recognizing a defect or disposing of non-sterile/non-safe accessories. Hence, in a particular instance, it is desirable that use of an electrosurgical handpiece be controlled to ensure its safe use. An important application of this principle is to avoid repeated use of the same handpiece. This is especially important in its application to non-ablative surgery, an example of which is described in our co-pending application Ser. No. 11/546,850, filed Oct. 13, 2006, the contents of which are herein incorporated by reference. In this application, which is non-invasive, the appearance of the electrode may not materially change after use, though it becomes non-sterile, and so the possibility exists of the surgeon inadvertently reusing the handpiece with the same electrode on a different patient. This problem can be overcome by making the handpiece disposable, intended for only a single use. But even if sold as a disposable handpiece, there remains the possibility that the handpiece will be reused with the same electrode or with a different electrode, as most handpieces allow electrode replacements.

SUMMARY OF INVENTION

An object of the invention is a disposable handpiece that after a certain period of time becomes unusable.

Another object of the invention is a disposable handpiece that does not allow replacement electrodes.

Still another object of the invention is a disposable handpiece incorporating a built-in lifetime-limiting device upon whose expiration the handpiece becomes unusable.

A further object of the invention is a disposable handpiece that is simple and economical to manufacture.

These and other objects of the invention are achieved in accordance with a feature of the invention by incorporating into the handpiece a device configured to disable the handpiece when a built-in usage time period expires.

In accordance with a preferred embodiment, the device comprises a timer in the form of an activating battery with a known discharge rate such that the battery voltage gradually reduces in value with use. The battery in turn is coupled to a circuit which monitors the battery voltage and operates a switch which decouples the handpiece electrode from the electrosurgical current source when the battery voltage falls below a preset value. This effectively disables the handpiece preventing reuse.

In a preferred embodiment, the battery is activated by the user which enables the handpiece for use. When the battery reaches a predetermined voltage lower than its nominal value, say, for example, 7 volts after about 1.5 hours for a 12 volt battery, the battery voltage monitoring circuit automatically cuts off the RF power so that the handpiece can no longer be used. The circuit is preferably engaged when the user pulls out a plastic tab which blocks the circuit from being complete.

[The Heart of the timer is the Seiko S-1000 Voltage Detector. The detector monitors the battery voltage and when the voltage drops below 7 volts it will disable the driver for the indicator and the RF Relay, preventing the RF from the radio-surgical generator from reaching the electrode. The timer is the time the battery takes to discharge from 12 volts to 7 volts; this is typically 1½ hours.]

The various features of novelty which characterize the invention are pointed out with particularity in the claims annexed to and forming a part of this disclosure. For a better understanding of the invention, its operating advantages and specific objects attained by its use, reference should be had to the accompanying drawings and descriptive matter in which there are illustrated and described the preferred embodiments of the invention, like reference numerals or letters signifying the same or similar components.

SUMMARY OF THE DRAWINGS

In the drawings:

FIG. 1 is a perspective view of one form of a disposable handpiece in accordance with the invention;

FIG. 2 is a top view of the disposable handpiece of FIG. 1;

FIG. 3 is a cross-sectional view along the line 3-3 of the handpiece of FIG. 2 showing the inside of the disposable handpiece of FIG. 2;

FIGS. 4 and 5 are a block diagram and circuit schematic, respectively, of the electronics of the disposable handpiece of FIG. 1.

DETAILED DESCRIPTION OF PREFERRED EMBODIMENTS

Our co-pending application Ser. No. 11/546,850, describes a non-invasive procedure for cosmetic skin surfacing using a monopolar handpiece with a dome-shaped electrode. FIGS. 1-3 illustrate one form of monopolar handpiece 10 that is disposable in accordance with the invention. The handpiece of FIGS. 1-3 can be used with conventional electrosurgical instruments, one example being the SURGITRON unit manufactured by Ellman International, Inc. of Oceanside, N.Y., and described in detail in U.S. Pat. No. 6,652,514. Such units are well known in the art and generate on command typically three radio-frequency (RF) modulated waveforms at for example 4 MHz frequency for use in surgical procedures for cutting tissue or coagulating bleeders or other non-invasive medical purposes. The RF energy is delivered to the surgical site via a handpiece such as the monopolar handpiece illustrated. The handpiece 10 is typically connected by a cable connector 12, shown at the right of FIG. 1, to an output connector 8 (see FIG. 5) on the face of the electrosurgical unit. The cable 12 in turn is connected via an inner conductor shown at the right at 14 and at the center at 16 to a circuit board 18 and via the latter to a contact terminal 20 of a relay 22, the other contact 24 of which is connected directly to an electrode 26 fixedly mounted at the front or distal end of the handpiece 10. The handpiece 10 is enclosed in a sealed enclosure serving as a handle portion 27 to which the user has no access, except by a pull tab 28. The relay 22, a commercial component, has 4 terminals, two of which 20, 24 already discussed provide a circuit conducting the main RF electrosurgical currents from the cable 12 to the electrode 26. The other two, not shown in FIG. 3, are shown at 30, 32 in the schematic of FIG. 5 and provide access to a solenoid coil 34 of the relay 22. The handpiece housing 27 is sealed and the electrode 26 is fixedly mounted to the housing illustrated at 36. The electrode in turn is permanently connected to the contact 24 as by crimping or soldering. As illustrated in FIG. 3, a battery 38 is mounted between two battery contacts, except that the end of a non-conductive pull tab 28 is positioned between a battery terminal and the contact, so that the battery 38 is isolated from the circuit. The pull tab 28 exits from the unit via a slot 40 in the handpiece housing wall. When the pull tab 28 is pulled out by the user, the battery makes contact and the circuit of FIG. 5 is activated.

The circuit of FIGS. 4 and 5 is configured to monitor the voltage of a discharging voltage source, that has a known discharge rate, which when enabled has activated a relay to complete the circuit for RF electrosurgical currents from the electrosurgical instrument to the handpiece electrode, and upon the voltage source falling to a predetermined value to deactivate the relay and interrupt the RF electrosurgical current circuit, with the result that the handpiece becomes disabled and no longer usable for applying RF currents to the surgical site.

A block diagram of one form of the circuit is illustrated in FIG. 4. A commercial battery 38 with a known discharge rate is connected to a voltage detector 42, another commercially-available component. When the circuit is activated, by the user pulling the pull-tab 28, via a driver 44 the RF relay 22 is energized, closing via its contacts 20, 24 the RF circuit allowing RF electrosurgical currents from the RF generator 8 to flow to the electrode 26. When the voltage detector 42 has detected that the battery voltage has dropped to a certain value, the driver 44 is deactivated which in turn deactivates the relay 22 whose contacts are in the RF electrosurgical current path thus disabling the handpiece.

The detailed schematic of FIG. 5 shows more clearly the operation. Connected across the battery 38 is a pair of resistors 50, 52 whose combined value primarily determines the discharge rate of the battery. Also connected in parallel across the battery are an MOS power transistor 44 and a LED indicator 54. The voltage detector 42 is connected between a midpoint of the resistors 50, 52 and the body contact of the transistor 44. While the battery is at its nominal voltage value and is slowly discharging to a lower value, say from 12 volts to 6-7 volts, the voltage detector 42 is normally OFF, the transistor 44 is normally ON, the LED is ON indicating that the handpiece is usable, and the relay coil 34 conducts the transistor current closing the relay contacts 20, 24 thus enabling the RF circuit. When the battery voltage drops to the predetermined value, the voltage detector 42 is activated shorting to ground its output terminal 56. This action turns OFF the transistor 44, which in turn deactivates the relay 22 and opens the contacts 20, 24, the indicator 54 turning OFF. The RF electrosurgical current circuit is thus disabled and the handpiece no longer usable. With a commercially available 12 volt battery, the circuit parameters can be easily chosen to cause the monitored battery voltage to reach a value of about 6-7 volts in about 1-2 hours. This is more than sufficient time for the average procedure to be completed, especially a procedure which involves a non-ablative skin cosmetic procedure as described in the referenced patent application. Once disabled, the user can no longer enable the handpiece and thus the disposable requirements of this handpiece can be satisfied. The handpiece enclosure being non-accessible by the user, the battery cannot be replaced and thus a new cycle initiated. The operation of the lifetime-controlling mechanism of the invention is independent of the RF instrument and of the user. Once activated, the handpiece lifecycle is automatically implemented and the handpiece is guaranteed to be unusable after the built-in time period has expired.

The handpiece itself is surprisingly inexpensive to manufacture. Virtually all of the electronic components are inexpensive, including the battery and the relay. The components are easily assembled into one half of the enclosure, and sealed to the second half after the electrode has been added.

In this way, the electrosurgical RF power energy is not supplied to the active handpiece until the lifetime-monitoring device has been activated ensuring that the handpiece and electrosurgical electrode are within their safe use term.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A disposable electrosurgical handpiece comprising:
   a) a sealed enclosure having at one end means for connecting to an RF cable and at the opposite end an electrosurgical electrode,
   b) inside the enclosure are:
      i. an activating voltage source whose output voltage is time dependent,
      ii. a voltage detector connect to the voltage source for monitoring its output voltage,
      iii. a switch actuable by the voltage detector upon the output voltage reaching a predetermined value,
      iv. the switch including a circuit electrically connecting the RF cable to the electrosurgical electrode,
   c) means accessible from outside the enclosure for activating the voltage source such that the switch circuit electrically connecting the RF cable to the electrosurgical electrode is enabled,
   d) the switch circuit electrically connecting the RF cable to the electrosurgical electrode becoming disabled upon the output voltage reaching its predetermined value after a certain time period has elapsed.

2. The disposable electrosurgical handpiece as claimed in claim 1, wherein the activating voltage source is a battery.

3. The disposable electrosurgical handpiece as claimed in claim 2, wherein a fixed load is connected across the battery such that its output voltage exhibits a known discharge rate.

4. The disposable electrosurgical handpiece as claimed in claim 1, wherein the enclosure seals off the activating voltage source.

5. The disposable electrosurgical handpiece as claimed in claim 1, wherein the means of claim element c) comprises a pull tab connected to the battery for activating the battery when pulled.

6. The disposable electrosurgical handpiece as claimed in claim 1, wherein the switch comprises a relay having contacts when closed electrically connecting the RF cable to the electrosurgical electrode, the relay including an activating coil for the contacts.

7. The disposable electrosurgical handpiece as claimed in claim 6, wherein a driver transistor is connected between the voltage detector and the relay activating coil.

8. The disposable electrosurgical handpiece as claimed in claim 7, further comprising a light indicator connected to the transistor and activated when the transistor is activated.

9. The disposable electrosurgical handpiece as claimed in claim 1, wherein the electrode is fixed to the enclosure.

10. A method for limiting the lifetime of an electrosurgical handpiece having an RF circuit connecting a cable connector at one end to an electrode at the opposite end, comprising:
   a. providing inside the handpiece a voltage source having a controlled reduction of output voltage as a function of time,
   b. providing means for a user to connect the voltage source to and to enable the RF circuit thereby enabling the handpiece, the connected voltage source's output voltage reducing as time elapses,
   c. monitoring the voltage source's output voltage while the handpiece is enabled,
   d. automatically disconnecting the RF circuit to disable the handpiece upon the voltage source's output voltage having fallen to a predetermined value.

* * * * *